(12) United States Patent
Shachar et al.

(10) Patent No.: US 9,329,173 B2
(45) Date of Patent: *May 3, 2016

(54) **METHOD AND APPARATUS FOR FORMING OF AN AUTOMATED SAMPLING DEVICE FOR THE DETECTION OF *SALMONELLA ENTERICA* UTILIZING AN ELECTROCHEMICAL APTAMER BIOSENSOR**

(75) Inventors: Yehoshua Shachar, Santa Monica, CA (US); Winston Wu, Alhambra, CA (US); Thomas Chen, La Canada, CA (US); Leslie Farkas, Ojai, CA (US); Brett Jordan, Los Angeles, CA (US); Paladin Luboff, Santa Monica, CA (US); Herwin Chan, Los Angeles, CA (US); Kyle Zimmerman, Los Angeles, CA (US)

(73) Assignee: Sensor-Kinesis Corporation, Los Angeles, CA (US)

( * ) Notice: Subject to any disclaimer, the term of this patent is extended or adjusted under 35 U.S.C. 154(b) by 1383 days.

This patent is subject to a terminal disclaimer.

(21) Appl. No.: 12/684,025

(22) Filed: Jan. 7, 2010

(65) Prior Publication Data

US 2011/0166033 A1 Jul. 7, 2011

(51) Int. Cl.
*C40B 30/04* (2006.01)
*G01N 33/53* (2006.01)
*G01N 33/543* (2006.01)
*G01N 33/569* (2006.01)

(52) U.S. Cl.
CPC ........ *G01N 33/5308* (2013.01); *G01N 33/5438* (2013.01); *G01N 33/56916* (2013.01); *G01N 2333/255* (2013.01)

(58) Field of Classification Search
CPC ..................................... C40B 30/04
USPC .............. 506/9, 39; 435/6.1, 7.1, 91.1, 91.31; 536/23.1, 24.32
See application file for complete search history.

(56) References Cited

U.S. PATENT DOCUMENTS

| | | | |
|---|---|---|---|
| 5,510,241 A | 4/1996 | Thorns | |
| 5,582,981 A | 12/1996 | Toole et al. | |
| 5,635,617 A | 6/1997 | Doran et al. | |
| 5,712,170 A | 1/1998 | Kouvonen et al. | |
| 5,840,867 A | 11/1998 | Toole et al. | |
| 6,680,377 B1 | 1/2004 | Stanton et al. | |
| 8,145,434 B2* | 3/2012 | Shachar et al. | 702/19 |
| 2005/0136419 A1* | 6/2005 | Lee | 435/6 |
| 2005/0176940 A1* | 8/2005 | King | 536/23.1 |
| 2005/0232747 A1* | 10/2005 | Brackmann et al. | 414/803 |
| 2007/0292941 A1* | 12/2007 | Handique et al. | 435/288.7 |
| 2008/0254446 A1* | 10/2008 | Sode et al. | 435/6 |
| 2011/0053283 A1* | 3/2011 | Hood et al. | 436/104 |

OTHER PUBLICATIONS

Sampson et al., ("Interdigited array microelectrode capacitive sensor for detection of paraffinophilic Mycobacteria", Proc. of SPIE, vol. 6886, 68860X, (2008), 0277-786).*
Varshney et al., ("A label-free, microfluidics and interdigitated array microelectrode-based impedance biosensor in combination with nanoparticles immunoseparation for detection of *Escherichia coli* O157:H7 in food samples", Sensors and Actuators B, 128, (2007), 99-107).*
Yang et al, ("Interdigited Array Microelectrode-based Electrochemical Impedance Immunosensor for Detection of *Escherichia coli* O157:H7", Anal. Chem, 2004, 76 1107-1113).*
Shabani et al. ("Bacteriophage-Modified Microarrays for the Direct Impedimetric Detection of Bacteria", Anal. Chem, 2008, 80, 9475-9482).*
Mahan et al. ("Bacteriophage P22 Transduction of Integrated Plasmids: Single-Step Cloning of *Salmonella typhimurium* Gene Fusions" Journal of Bacteriology, Nov. 1993, p. 7086-7091).*
Munoz-Berbel et al., ("Impedance-based Biosensors for pathogen Detection", Chapter 15, pp. 341-376, "Principals of bacterial detection: Biosensors, Recognition Receptors, and Microsystems" Springer Science and Business Media, 2008).*
Sampson et al. ("Interdigitated array microelectrode capacitive sensor for detection of paraffinophilic Mycobacteria", Proc. of SPIE, (2008), vol. 6886, pp. 277-786).*
Varshney et al., ("A label-free, microfluidics and interdigitated array microelectrode-based impedance biosensor in combination with nanoparticles immunoseparation for detection of *Escherichia coli* O157:H7 in food samples", Sensors and Actuators B, (2007), vol. 128, pp. 99-107).*
Sampson et al. (Proc. of SPIE, 2008, vol. 6886, pp. 68860x1-8, "Interdigited array microelectrode capacitive sensor for detection of paraffinophilic Mycobacteria").*
Varshney et al. (Sensors and Actuators B, 2007, vol. 128, pp. 99-107, "A Label-free, microfluidics and interdigitated array microelectrode-based impedance biosensor in combination with nanoparticles immunoseparation for detection of *Escherichia coli* O157:H7 in food samples").*

(Continued)

*Primary Examiner* — Jane Zara
(74) *Attorney, Agent, or Firm* — Marcus C. Dawes; Daniel L. Dawes

(57) ABSTRACT

An aptamer-based solid-state electrochemical biosensor for label-free detection of *Salmonella enterica* serovars utilizing immobilized aptamers. The device is realized by forming a matrix array of parallel capacitors, thus allowing the realization of low-cost, portable, fully integrated devices. Protein-aptamer binding modulates the threshold voltage of a circuit, changing the impedance (capacitance) of the circuit. This circuit is further characterized by an electrode coded with a p-Si substrate, enhancing the affinity between the *Salmonella* outer membrane proteins (OMPs) and the aptamer. An aptamer embedded detection plate is configured within a testing lid device that fits a standard, commercially available polymer specimen jar. A sample is mixed with broth for incubation and cultivation of any present *Salmonella* bacteria to obtain acceptable concentration of the pathogen for testing. The information obtained can then be transmitted by wireless network.

13 Claims, 15 Drawing Sheets

(56) References Cited

OTHER PUBLICATIONS

Figure 1:
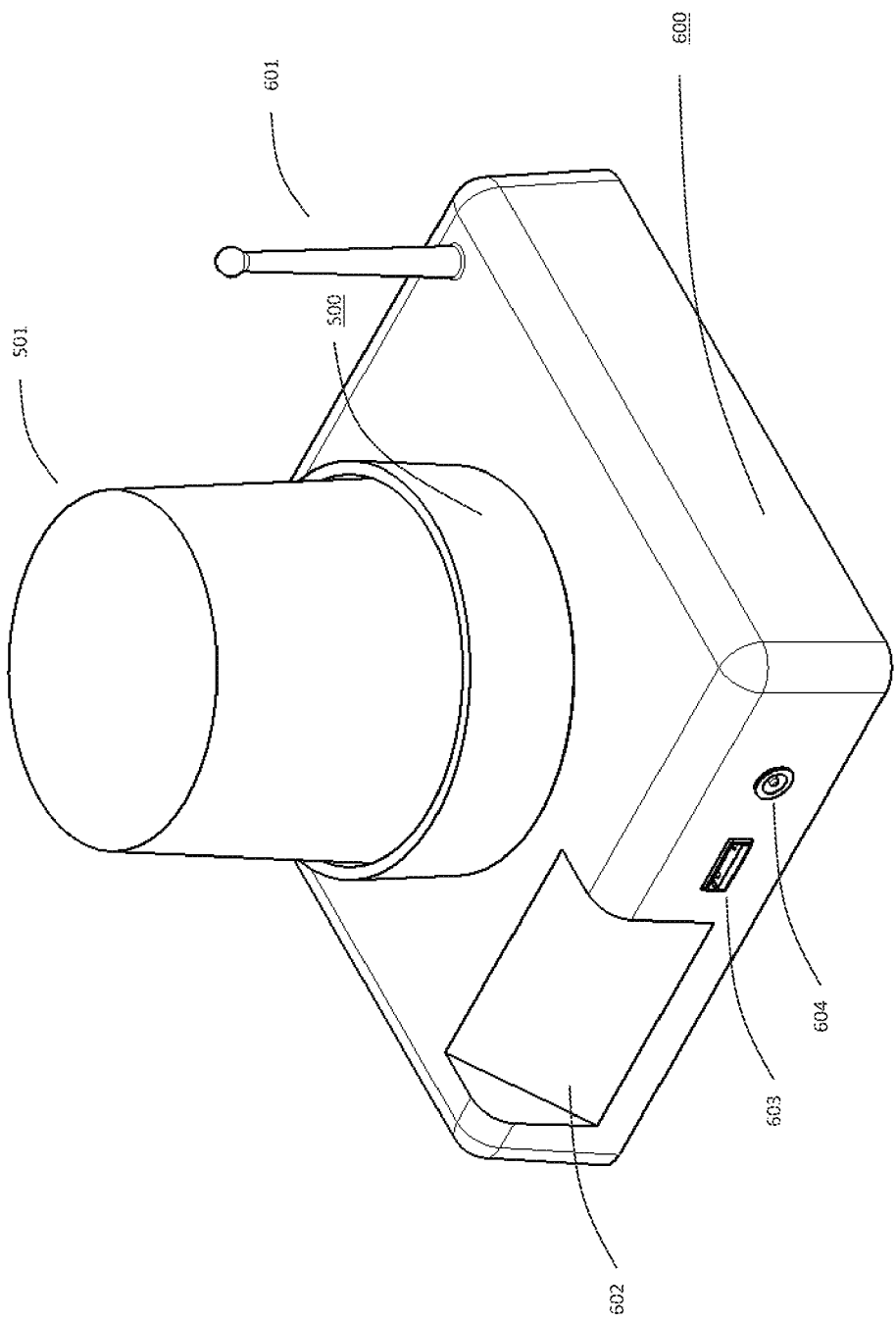

Yang et al. (Analytical Chemistry, 2004, vol. 76, pp. 1107-1113, "Interdigitated array microelectrode-based electrochemical impedance immunosensor for detection of *Escherichia coli* O157:H7").*

Shabani et al., (Analytical Chemistry, 2008, vol. 80, pp. 9475-9482, "Bacteriophage-modified microarrays for the direct Impedimetric detection of bacteria").*

Munoz-Berbel et al., (("Principals of bacterial detection: Biosensors, Recognition Receptors, and Microsystems", Springer Science and Business Media, 2008, "Impedance-based Biosensors for pathogen Detection", Chapter 15, pp. 341-376).*

Mahan et al., (Journal of Bacteriology, 1993, vol. 175, No. 21, pp. 7086-7091, "Bacteriophage P22 Transduction of Integrated plasmids: single-step cloning of *Salmonella typhimurium* gene fusions").*

Zelada-Guillen et al., (Angewandte Chemie International Edition, 2009, vol. 48, pp. 7334-7337, "Immediate detection of living bacteria at ultralow concentrations using a carbon nanotube based potentiometric aptasensor").*

Joshi et al. (Molecular and Cellular Probes, 2009, vol. 23, pp. 20-28, "Selection, characterization, and application of DNA aptamers for the capture and detection of *Salmonella enterica* serovars").*

Brenner et al. (Journal of Clinical Microbiology, vol. 38, No. 7, pp. 2465-2467, "*Salmonella* Nomenclature").*

\* cited by examiner

METHOD AND APPARATUS FOR FORMING OF AN AUTOMATED SAMPLING DEVICE FOR THE DETECTION OF *SALMONELLA ENTERICA* UTILIZING AN ELECTROCHEMICAL APTAMER BIOSENSOR

RELATED APPLICATIONS

The application is related to co-pending U.S. patent application Ser. No. 12/422,125, titled 'Method and Apparatus for Forming a Homeostatic Loop Employing an Aptamer Biosensor', filed Apr. 10, 2009.

BACKGROUND OF THE INVENTION

1. Field of the Invention

The invention relates to the field of chemical biosensors, specifically the use of electrochemical aptamer biosensors utilized in an automated in situ test for the presence of *Salmonella enterica* bacteria.

2. Description of the Prior Art

*Salmonella* is a genus of rod-shaped, gram-negative, non-spore forming, and predominantly motile enterobacteria. Salmonellae are a significant cause of food borne illness worldwide. Around 1.4 million cases of salmonellosis are reported annually in the US, with approximately 16,000 hospitalizations and 550 deaths. *Salmonella* alone is associated with 26% of all the food borne diarrheal cases leading to hospitalization. *Salmonella* bacteria are especially dangerous to humans because of their zoonotic nature, meaning that they have the ability to infect across several species.

Enteritis *Salmonella* (e.g. *Salmonella enterica*) can cause diarrhea, which usually does not require antibiotic treatment. But people at risk such as infants, HIV patients, small children, the elderly, and those with suppressed immunity can become seriously ill. Osteomyelitis may develop in children with sickle cell anemia who are infected with *Salmonella*. *Salmonella* bacteria is capable of causing typhoid fever. This infects over 16 million people worldwide each year, with 500,000 to 600,000 of these cases proving to be fatal, according to the World Health Organization.

*Salmonella* can survive for weeks outside a living body. Ultraviolet radiation and heat accelerate their demise; they perish after being heated to 55° C. (131° F.) for one hour, or to 60° C. (140° F.) for half an hour. They have been found in dried excrement after over 2.5 years. To protect the population from *Salmonella* infection, governments and other rule-making bodies have enacted many rules regarding the handling of food. For cooking at home, it is recommended that food be heated for at least ten minutes at 75° C. (167° F.) at the center of the food that is being prepared. *Salmonella* is not destroyed by freezing.

Because of this, there have been many attempts to control the spread of *Salmonella* bacteria in the food supply. One method of this is to disseminate information on proper food handling and cooking techniques. This is done by a wide variety of rules and regulations regarding the production, shipping, and handling of food.

One aspect of food regulation is determining acceptable levels of *Salmonella* bacteria in food products. The USFDA has, for example, set an acceptable level for *Salmonella* in the water supply as not greater than 3 cfu/4 gm. (www.fda.gov.)

Of particular concern is salmonellosis caused by multidrug resistant (MDR) strains such as *Salmonella enterica* serovar Typhimurium DT104 or *S. enterica* serovar Newport. Drug resistant strains are, by their nature, much more difficult to treat than other strains of *Salmonella*. They can be particularly devastating to at-risk groups, such as infants and the elderly. It is in the case of MDR strains of *Salmonella* especially that it is important to have accurate, easy to administer testing of food sources. In this way, the initial transmission of the pathogen to humans can be reduced or eliminated.

Because of the great need for accurate testing for the presence of *Salmonella*, there are many testing methods available today commercially. The USFDA has guidelines for testing (see USFDA Setting a Risk Threshold for Enteric Diseases in Drinking Water), as has the USDA (see *Salmonella* Testing). Testing is traditionally accomplished either through DNA based methods (e.g. GENE-TRAK Colorimetric, and TAQ-MAN ® by PE Applied Biosystems), through Immunoassay based methods (e.g. EIA FOSS™ by Foss Electric), through immuno-latex aggulation based methods (e.g. SPECTATE ® by May & Baker Diagnostics Ltd.), and also sometimes through other biochemical methods such as a motility detection system (e.g. SALMONELLA RAPID TEST® by Oxoid).

These tests are widely used and accurate, but some can take many days to accomplish, and many of these tests are not highly automated, namely they all rely on the technician to determine the outcome of the test. Additionally, these tests are accomplished at a certain point of time, often by in-lab enrichment of the bacterial sample.

Aptamers are well known in the field for their ability to bind to specific substances. Nucleic acid based aptamers are highly stable also. Aptamer specificity is often determined utilizing the systematic evolution of ligands by exponential enrichment method. This allows for high specificity to a wide variety of molecules. Aptamers are now gaining use as markers and linkers to cells. Aptamers are able to bind to the outer membrane proteins of cells and therefore act as markers and binders to the cell. (Joshua K. Herr et al., Aptamer -Conjugated Nanoparticles for Selective Collection and Detection of Cancer Cells , Analytical Chemistry, Vol. 78, No. 9, pp.2918-2924, May 2006.)

Utilizing aptamer binding to *Salmonella enterica* has undergone proof of principle testing under Raghavendra Joshi et al. (Raghavendra Joshi et al., *Selection, characterization, and application of DNA aptamers for the capture and detection of Salmonella enterica serovars*, Molecular and Cellular Probes, Vol. 23, pp. 20-28, 2009). In those experiments, two highly specific *Salmonella enterica* aptamers were discovered.

By utilizing the two discovered sequenced aptamers, Joshi et al, were able to utilize aptamer-infused magnetic particles to separate and concentrate *Salmonella enterica* bacteria in a sample.

U.S. Pat. No. 5,510,241 ("Thorns") discloses a testing system for *Salmonella* bacteria, but does so utilizing monoclonal antibodies.

U.S. Pat. No. 5,582,981 ("Toole et al.") discloses use of aptamer technology for binding to specific substances, but utilizes polymerase chain reaction. PCR testing requires a laboratory environment and a trained technician.

U.S. Pat. No. 5,635,617 ("Doran et al.") discloses a specific target gene and protein of *Salmonella* bacteria; however, it does not apply this to a procedure for automated testing for the pathogen in food.

U.S. Pat. No. 5,712,17 ("Kouvonen et al.") discloses a rapid immunoassay test strip that could be utilized for testing for pathogens, but does not disclose a way to do so in an automated way, and Kouvonen's method further requires a trained technician to accomplish the testing.

U.S. Pat. No. 5,840,867 ("Toole et al.") discloses several specific aptamer sequences that may be utilized for targeting. However, it does not disclose a specific method for their use, nor does it disclose an aptamer specific to *Salmonella enterica* outer membrane proteins.

U.S. Pat. No. 6,680,377 B1 ("Stanton et al.") discloses the composition of aptamers as beacons. Because this is not an electrochemical feedback system, it requires trained lab personnel and lab equipment. Also, this piece of prior art does not disclose a detection system for *Salmonella enterica*.

What is needed in the field is a highly automated, accurate system that can be used outside of the laboratory environment, specifically at "Points-of-Inspection" such as ports, border check-points, and weighing stations along the Interstate Freeway System by lay practitioners to accurately test for the presence of *Salmonella* in food samples in situ.

BRIEF SUMMARY OF THE INVENTION

The disclosed invention and method provides a highly automated system for testing for *Salmonella enterica* bacteria. These testing procedures are highly automated so as to allow minimal training to be required in order to carry out the examination. Further, a method is disclosed herein for testing that allows results to be wirelessly transmitted while goods are in transit, allowing for quick processing at loading and unloading locations.

The device is formed from a standard polymer specimen cup attached to a specialized testing device lid. The testing device lid utilizes *Salmonella enterica* specific aptamers in a microfluidics electrochemical sensor array, allowing for testing results to be timed and interpreted by pre-programmed computer software. Use of microfluidic technology increases the sensitivity of the aptamer sensor array.

The testing device lid employs a standard Universal Serial Bus (USB) connector built into the external surface of the lid. Internally, the lid features an aptamer sensor array which optionally features a built-in micropump to ensure proper fluid circulation during testing. The aptamer sensor array is built into a printed circuit board (PCB) that allows for control of the sensor array. The PCB also includes a temperature sensor. Temperature sensor readings are periodically tracked by a software algorithm to accurately predict the state of the testing process.

The base of the device utilizes a USB connection to connect to the testing device lid. Embodied in the base station of the invention is a wireless antenna for communication of testing results to WiFi computer networks often available at shipping yards. There is an additional USB connection on the front of the device, allowing the base station to be programmed by a standard desktop computer with appropriate compatible software. Further, this USB connection may be utilized to connect and upgrade the device, providing an additional externalized battery supply for long voyages, or by up-linking to a cellular phone or sat-phone capable device to provide worldwide network access to the testing unit.

The base of the device utilizes a standard Liquid Crystal Display (LCD) screen to output visually the state and results of the testing procedure without the need to connect to a standard personal computer. A PCB board features a central processing unit, flash memory for storage, and other components needed to provide proper running protocols for the device. The base station also utilizes standard rechargeable C sized or like batteries as a power source when needed. A plug-in device to recharge the batteries is located on the front of the base station adjacent to the LCD screen.

The device is utilized by adding a small amount of commercially available broth (such as BHI broth) to the sterile standard specimen cup, removing the optional plastic covering protecting the aptamer sensor plate, adding a sample of the food to be tested, and then subsequently firmly attaching the testing device lid to the specimen cup. The cup and lid is then turned upside-down and placed in this orientation upon the base station. The base station utilizes an always on real-time clock. Based upon the ambient temperature and time, the protocols designed into the base station will analyze the sample at the appropriate times to ensure accurate measure.

After the broth is added to the specimen cup, the sample is added. Incubation is accomplished at ambient temperature to increase the bacterial load to testable levels. The programming of the unit allows for independent calculation of the length needed to test the *Salmonella* bacterial load in the sample.

Accordingly, the present invention may have one or more of the following advantages:

It is therefore an embodiment of the invention to allow for a simple and highly automated procedure for testing for *Salmonella enterica* bacteria by utilizing a standard specimen cup with a specially designed testing device lid.

It is a further embodiment of the invention that the calculation of the testing for *Salmonella enterica* bacterial be accomplished in a base station device incorporating temperature and aptamer biosensor data from the cup, and to provide an accurate measurement of the progress of the testing procedure.

It is yet another embodiment of the invention that the base station device is enabled with wireless capability to allow in situ inspection of data from testing.

It is another embodiment of the invention that it may be powered by battery, by DC current from a truck or car, or by AC current from a wall socket or other source.

In a further embodiment of the invention, once the sampling process is completed, the device may be attached externally to a shipping container in a case. This case may be bolted, welded, or magnetically attached to the outside of a container.

It is another embodiment of the invention that the test may be started at the first point of shipment, and that the testing unit may follow that cargo container. In this way, regardless of the testing time needed, the testing time overlaps with the travel time of the cargo. Utilizing this method, many shipments would have completed their test for *Salmonella* before they reach their destination, thereby making the authorization of the shipment more efficient.

It is another embodiment of the invention that data could be harvested from the automated testing device at wireless access points located at Points-of-Inspection, providing real-time access to the data. One example of the use of this for practical purposes follows. A trucker hauling spinach with the device analyzing a sample during transit could drive through a weigh station where there is WiFi access. At that time, if the sample is deemed tainted, the central office for the shipment company could be notified via the internet, and the central office would notify the trucker to take the tainted spinach to an alternative site because it is no longer fit for human consumption. Connection between the analyzer unit and the central office could be further heightened by connecting the base station to a cell phone or satellite phone connection via the USB port on the front of the base station.

It is finally an embodiment of the invention that data is collected over time, allowing for aggregation of *Salmonella*

*enterica* bacterial growth to be recorded over the time of each shipment, allowing for more detailed studies to be performed regarding food spoilage.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 1 is a perspective externalized view of the apparatus.

FIG. 2A is an external view of the specimen cup and testing lid device with a clear view of the docking hole and USB docking port connection between the specimen cup lid and the base.

FIG. 2B is an alternate external view of the of the specimen cup, highlighting the electrochemical aptamer testing site placement upon inside of the lid device.

FIG. 2C is a side view of the internal components of the testing lid device for the specimen cup, highlighting the aptamer sensor plate attached to the PCB, and the USB connection.

FIG. 2D is a perspective view of the printed circuit board with attached aptamer electrochemical sensor plate, present within the testing lid device of the invention. The temperature sensing chip is visible on the PCB.

FIG. 2E depicts the reverse side of the printed circuit board shown in FIG. 2D and an array of electrodes coded with *Salmonella* sensors forming a series of grooved capacitive plates disposed thereon.

FIG. 3 is a perspective view of the base unit, with internal components visible. The PCB, wireless antennae, output display screen, and data connection port can be viewed in this drawing.

FIG. 4A is a cross section of an isometric view of the capacitive arrangement of the *Salmonella* detector.

FIG. 4B is a graphic depiction of the *Salmonella* sensor hybridization element.

FIG. 4C is a graphic depiction of the *Salmonella* sensor hybridization element, including a depiction of the structure and nucleotide sequence.

FIG. 5 is a cross-section of the apparatus with a schematic representation of the electrical detection module.

FIG. 6 is a schematic representation of the preferred embodiment of the invention depicting one cell of an equivalent electrode-electrolyte node from the capacitor array.

FIG. 7 is a schematic representation of the capacitor matrix array depicting the equivalent circuit.

FIG. 8 is a possible layout of the temperature sensor, which is a component of the lid assembly, of the unit.

FIG. 9 is a schematic block diagram of the computations performed by the Central Processing Unit on the printed circuit board in the base of the invention.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

Definitions

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention; the methods, devices, and materials are now described. All publications mentioned herein are incorporated herein by reference for the purpose of describing and disclosing the materials and methodologies which are reported in the publications which might be used in connection with the invention. Nothing herein is to be construed as an admission that the invention is not entitled to antedate such disclosure by virtue of prior invention.

"Serovar" or "Serotype" are both short forms of referring to the serological variants of *Salmonella* bacteria. The particular serovar of a *Salmonella* strain refers to the individual classification of that bacteria within the genus, as based upon cell membrane antigens. Serotyping often plays an essential role in determining species and subspecies. The *Salmonella* genus of bacteria, for example, has been determined to have over 4400 serotypes, including *Salmonella enterica* serovar Typhimurium, *S. enterica* serovar Typhi, and *S. enterica* serovar Dublin.

Pathogen as used herein refers to a biological agent that causes disease or illness to its host.

Electrochemistry as used herein refers to a branch of chemistry that studies chemical reactions which take place in a solution at the interface of an electron conductor (a metal or a semiconductor) and an ionic conductor (the electrolyte), and which involve electron transfer between the electrode and the electrolyte or species in solution.

Aptamer as used herein refers to oligonucleic acids or peptide molecules that bind to a specific target molecule.

*Salmonella* as used herein refers to a genus of rod-shaped, predominantly motile, enterobacteria. It can be found in animal, human, and non-living habitats.

Pilus (plural Pili) as used herein refers to a hair-like appendage found on the surface of many bacteria. The terms pilus and fimbria are often used interchangeably, although some researchers reserve the term pilus for the appendage required for bacterial conjugation. All pili are primarily composed of oligomeric pilin proteins.

IVB Pili as used herein refers to bacterial pili that generate motive forces.

Monocytic-Cell as used herein refers to a type of white blood cell, part of the human body's immune system.

Electrophoresis as used herein refers to the motion of dispersed particles relative to a fluid under the influence of a spatially uniform electric field.

Plasmon as used herein refers to a quantum of plasma oscillation. The plasmon is a quasiparticle resulting from the quantization of plasma oscillations just as photons and phonons are quantizations of light and sound waves, respectively.

"Surface modification" as used herein refer to the process of detailed by Y. Han et al., 2006 which describes preparing the $SiO_2$ surface, as it is cleaned with MeOH/HCl (1/1) for 30 minutes at room temperature, rinsed with ultra pure water (Milli-Q Gradient A10 18.2 MΩ, and dried with Argon. In the next step, the surface is modified with $NH_2$ groups by a silanization step with 3-aminopropyltriethoxysilane (APTES) either in the gas phase. For gas-phase silanization, the chips are placed in a desiccator containing a few drops of silane. The desiccator is sealed and heated above 100° C., and the chips were left to react for 1-2 hours under a low pressure (~1 mbar) with the silane vapor. This technique employs biocompatible scaffolds provide viable alternatives forming the prosthetic materials for adhesion. The use of self assembled peptide amphiphile nanofiber coated scaffold to grow the linker, is advantageous because of its high surface area, which permits a large number of sites for the succinic anhydride, adhesion and growth. (Succinic anhydride, also called dihydro-2,5-furandione, is an organic compound with the molecular formula $C_4H_4O_3$.) The fibrous nature of the coating allows the linker, to penetrate the surface by diffusion, and the matrices have sufficient surface area and exposure to the linker. The linker, is further combined with an amino-silanization. (The surface of a quartz or glass wafer ($SiO_2$ 14) is treated with different aminosilanes in solution where surface density increased sharply with the reaction time and produced the multilayer.) The amino-silanization, scaffolds provide viable alternatives forming the prosthetic materials for adhesion to the $SiO_2$ insulator surface/

"Aptamer immobilization" as used herein refer to the process detailed by Hyun-Seung Lee et al., 2009, which describes immobilization, whereby an Salmonella DNA aptamers named above are dissolved in phosphate buffer (PB, 200 mM, pH 8) to prepare aptamer solution at a concentration of 20 mM. Each vial is incubated at room temperature for 4 hours. After that, aptamer solution (500 μL) is added and incubated at pH 7.5 and room temperature. The resulting substrates are washed with phosphate buffer saline (PBS) and water in a sequential manner. Finally, the substrates are air-dried and the immobilization is analyzed by atomic force microscopy (AFM), indicating an average of ~3 nm increase of surface thickness due to the immobilization of Salmonella enterica aptamers.

The concept of using single-stranded nucleic acids (aptamers) as affinity molecules for protein binding was initially described in 1990 (Ellington and Szostak 1990, 1992; Tuerk and Gold 1990), and is based on the ability of short sequences to fold, in the presence of a target, into unique, three-dimensional structures that bind the target with high affinity and specificity. Eugene W. M Ng et al., 2006, describes that aptamers are oligonucleotide ligands that are selected for high-affinity binding to molecular targets.

"Fabrication of silicon insulator surface" as used herein refer to the process detailed by Hyun-Seung Lee et al., 2009, which describes a layer of Au (100 μm) deposited to form the interleaved array of electrodes 103, inside an insulating enclosure 17. Silicon crystal for p-doping 15 is grown on the Au conductor surface 16, with a constant flow of $SiH_4$ precursor at 530° C. under the gas pressure of 50 Torr. During this process, silicon crystals are in situ doped with $B_2H_6$ as p-dopants at the relative pressure ratio of $SiH_4:B_2H_6$ to be $10:1 \times 10^{-3}$. The flow of $SiH_4$ is continued but $B_2H_6$ is stopped when the p-substrate 15, reaches 1 μm. After the additional Si layer reaches 10 nm, the flow of $SiH_4$ is stopped; the temperature is raised to 820° C. and gas chamber is opened to the atmospheric pressure, allowing oxidation in the dry atmosphere to form the $SiO_2$ insulation layer.

"Capture reagent" as used herein, is a molecule or compound capable of binding the target analyte or target reagent, which can be directly or indirectly attached to a substantially solid material. The capture agent can be any substance for which there exists a naturally occurring target analyte (e.g., an antibody, polypeptide, DNA, RNA, cell, virus, etc.) or for which a target analyte can be prepared, and the capture reagent can bind to one or more target analytes in an assay.

"Target analyte" as used herein, is the substance to be detected in the test sample using the present invention. The analyte can be any substance for which there exists a naturally occurring capture reagent (e.g., an antibody, polypeptide, DNA, RNA, cell, virus, etc.) or for which a capture reagent can be prepared, and the target analyte can bind to one or more capture reagents in an assay. "Target analyte" also includes any antigenic substances, antibodies, and combinations thereof. The target analyte can include a protein, a peptide, an amino acid, a carbohydrate, a hormone, asteroid, a vitamin, a drug including those administered for therapeutic purposes as well as those administered for illicit purposes, a bacterium, a virus, and metabolites of or antibodies to any of the above substances.

"Target analyte-analog" as used herein, refers to a substance which cross reacts with an analyte capture reagent although it may do so to a greater or lesser extent than does the target analyte itself. The target analyte-analog can include a modified target analyte as well as a fragmented or synthetic portion of the target analyte molecule so long as the target analyte analog has at least one epitomic site in common with the target analyte of interest.

"Test sample" as used herein, means the electrolyte solution containing the target analyte to be detected and assayed using the present invention. The test sample can contain other components besides the target analyte, can have the physical attributes of a liquid, or a gas, and can be of any size or volume, including for example, a moving stream of liquid. The test sample can contain any substances other than the target analyte as long as the other substances do not interfere with the binding of the target analyte with the capture reagent or the specific binding of the first binding member to the second binding member. Examples of test samples include, but are not limited to: Serum, plasma, sputum, seminal fluid, urine, other body fluids, and environmental samples such as ground water or waste water, soil extracts, air and pesticide residues.

"Methods and reagents" used by authors for the purpose of analysis and testing of the proposed apparatus are based on information provided by Hyun-Seung Lee et al., 2009 paper. The following reagents were used without further purification for the propose of identifying the method: 3-Aminopropyl diethoxysilane (APDES), succinic anhydride (SA), sodium carbonate (SC), phosphate buffered saline (PBS) tablet, sodium dodecylsulfate (SDS), 1-ethyl-3-[3-(dimethylamino) propyl]carbodiimide (EDC), N-hydroxysulfo succinimide (sulfo-NHS), sodium hydroxide (NaOH), sodium chloride (NaCl) (Sigma-Aldrich Co. St. Louis, Mo.).

The "SELEX" process is used by this invention to mean a technique for screening a very large library of oligonucleotides with random sequences by iterative cycles of selection and amplification.

"Effective sensor geometry" is used by this invention to mean the physical geometry $G_x$ of the biosensor and the arrangement of its sensing structures that maximize the sensing area with minimum volume. The capacitance due to the sensor geometry $C_{geometry}$ is described in Equation 1 using the dielectric ($\in_r$) as a variable that correlates with target analyte concentration in the test sample.

$$C_{geometry} = \varepsilon_r \varepsilon_0 \frac{A}{d} \quad (1)$$

where $\in_r$ is the combined relative permittivity (dielectric constant) of the medium consisting of *Salmonella* bacteria, bodily fluid, Succinic anhydride linker, Amino hybridization substance, $SiO_2$ insulator, and p-Si substrate; $\in_0$ is the permittivity of the free space ($8.854\times10^{-12}$ F/m); A is the total area of electrode plates with width, and length; and d is the separation between the plates. The values of A and d are chosen so that the change in capacitance can be effectively measured with the following capacitance measurement technique.

For example, with the cross sectional area ($d_{cap}\times W_{cap}$) of the biosensor is approximately 1 cm×1 cm, which is broken into pairs of electrode plates arranged in a digitated fingers pattern, with every other electrode plate is tied to form two sets of plates. Following the insulator fabrication process described above, the combined thickness of one sensor plate is 102.02 μm (the sum of the thicknesses of electrode, two layers of p-substrate, two layers of insulator). With the plate area of 1 $cm^2$ providing capacitance of around 10 uF, the size of the plates A and the distance between the plates d can be adjusted to meet the requirements of the detection circuit. The only variable in Equation 1 is the combined dielectric constant $\in_r$ that changes with *Salmonella* bacteria molecule hybridization with the surface.

The "Measurement technique" of the electrochemical cell, as noted by FIGS. 1, 1A, 2, & 2A, is based on said sensing principle of a variable capacitor cell where the dielectric ($\in_r$) of the electrode/solution interface model, is the variable. In this model, the *Salmonella* bacteria outer membrain protein, *Salmonella enterica* aptamer, introduces additional insulating layers, between electrode and solution, resulting in a measurable change in capacitive component of the interface model. The charge-based capacitance measurement (CBCM) technique can measure this change in capacitive component of the electrode-solution interface impedance. The measurement principle of this CBCM technique is to charge and discharge the electrochemical cell at an appropriate frequency, and measure its equivalent capacitance from the average current in half-period, noted in Equation 2.

$$I_{avg} = \frac{\Delta Q}{T/2} = \frac{C\Delta V}{T/2} = 2C\Delta Vf \tag{2}$$

where ΔV and f are known and $I_{avg}$ can be measured. This measurement technique consists of two separate circuits. The Op Amp voltage follower increases the input impedance of the electrochemical cell so that the cell can be driven by a near perfect square wave, from a digital output signal line from a microcontroller. The frequency (f) of the square wave is chosen as the maximum frequency that completely charges and discharges the capacitor in the electrochemical cell in the half period. The second part converts $I_{avg}$, into voltage value with a known resistor value $R_1$, and amplified with an Op-Amp. $V_1$, at the output of the Op Amp, can be calculated as shown in Equation 3.

$$V_1 = -C_{cell}R_1\frac{dV_{in}}{dt} \tag{3}$$

An Op Amp integration circuit converts the transient voltage values, into a square wave, as shown in Equation 4.

$$V_{out} = -\frac{1}{C_2}\int\frac{V_1}{R_2}dt \tag{4}$$

Substituting Equation 2 into 3, the output of the above, as a function of its input can be calculated as shown in Equation 5 leading to Equation 6.

$$V_{out} = -\frac{1}{C_2R_2}\int -C_{cell}R_1\frac{dV_{in}}{dt}dt \tag{5}$$

$$V_{out} = \frac{C_{cell}R_1}{C_2R_2}V_{in} \tag{6}$$

The output voltage, which is sampled by an ADC, is proportional to the value of $C_{cell}$.

DETAILED DESCRIPTION OF THE PREFERRED EMBODIMENTS

The disclosed invention and method provides a highly automated system for testing for *Salmonella enterica* bacteria (2).

FIG. 1 shows an externalized view of the entire testing apparatus as a whole. A base station unit (600) utilizes a built-in LCD (602) for display of data. Examples of data shown would be progress of testing, current temperature, average temperature, current power level of the batteries, time to finishing of testing, and other such information. FIG. 1 exhibits a wireless antenna for data transmission (601), a standard USB connection (603) for data and power transfer to an externalized programming device such as a personal computer (not shown), and external power supply connector (604) for power which can be utilized from an AC or DC power source. An additional externalized battery (not shown) can be connected via the power port (604) or via the USB port (603) by means known in the art.

FIG. 2A depicts a testing device specimen cup (500) and lid (501). A USB communication port (406) within the lid (501) to the base station (600) is visible.

FIG. 2B is an inverted view of the liquid sealed container (500) for the food sample and container lid (501) that is shown in FIG. 2A. Because the orientation is changed in this view, a *Salmonella* aptamer sensor (502) coupled to the underside of the lid (501) is visible.

FIG. 2C shows the container lid (501) and its internalized components. The USB connection (406) is visible again, and is shown coupled to a Printed Circuit Board (PCB) (400) in the lid (501). Also coupled to the underside of the PCB (400) in the lid (501) is a *Salmonella* aptamer sensor (502).

FIG. 2D is a perspective view of the PCB (400) coupled within the lid (501) and the coupled *Salmonella* aptamer sensor (502). FIG. 2E depicts the reverse side of the PCB (400) shown in FIG. 2D. In FIG. 2E, the PCB (400) and an array of electrodes coded with *Salmonella* sensors forming capacitive plates (103) is seen. Note that these sensors are grooved. In this configuration, no pumping device is needed inside the sample cup (500) to assist the aptamer sensors (502) with proper flow. However, it should be expressly understood that a pumping device can be added as an alternative embodiment of the invention to improve flow without departing from the original spirit and scope of the invention.

FIG. 3 shows a preferred embodiment of the internal components of the base station unit (600). The wireless antenna (601) is shown again, along with the LCD (602), USB connection (603), and power port (604), as previously described. In addition, a base PCB (610) in the base station (600) is visible, which houses a CPU, flash memory, and other solid state components of the base station (600). A plurality of batteries (615) are also comprised within the base station (6000. Here it is envisioned that two C size rechargeable batteries known in the art may be used, but other battery power sources or sizes can be used without straying from the scope of the invention.

Figure 4A:
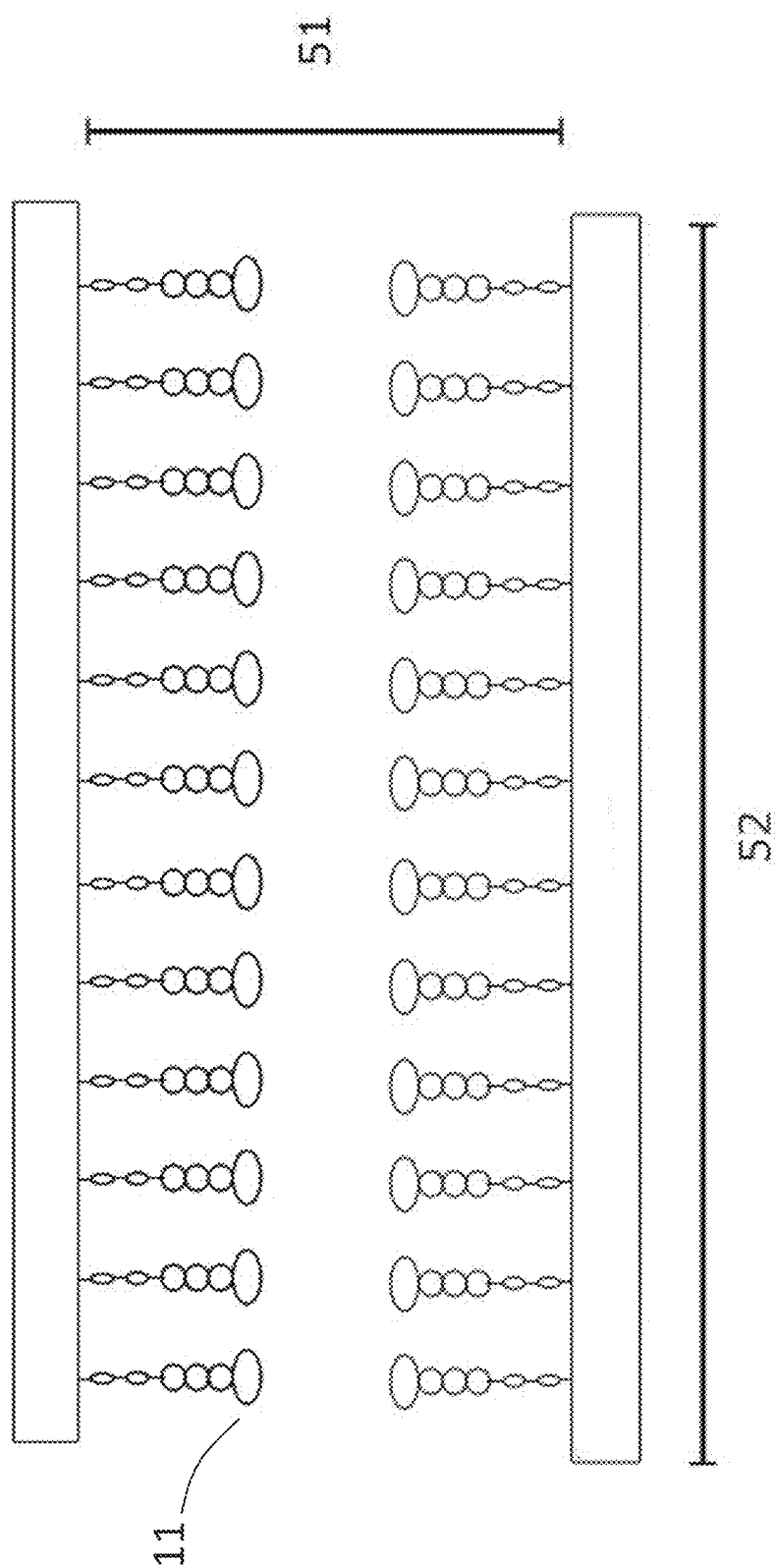

FIG. 4A depicts the width (Wcap) (52) of the *Salmonella* aptamer sensors (502) and the relative distance (Dcap) (51) between the aptamer sensors (502). These gaps (51, 52) are important in determining proper capacitance for the sensing of the presence of *Salmonella enterica* bacteria.

Figure 4B:
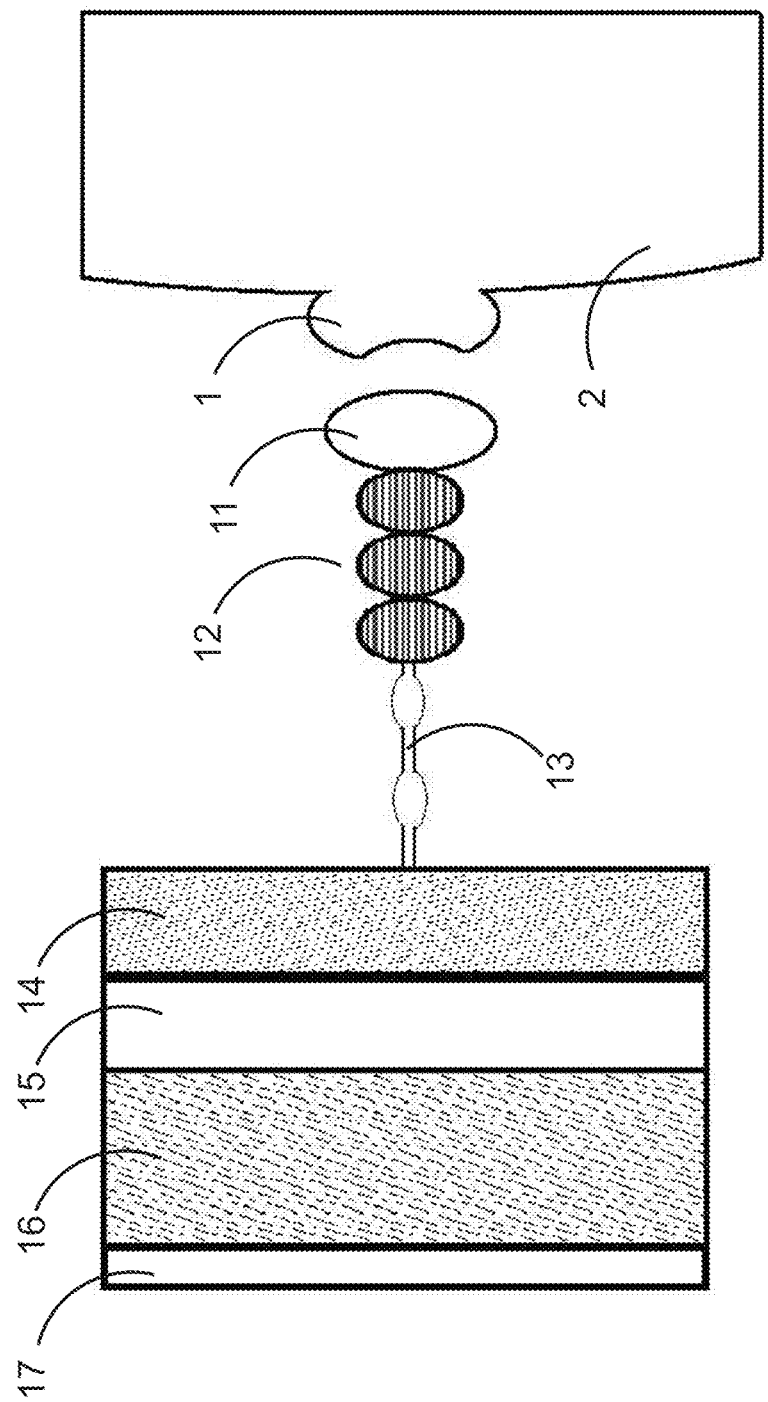
Figure 4C:
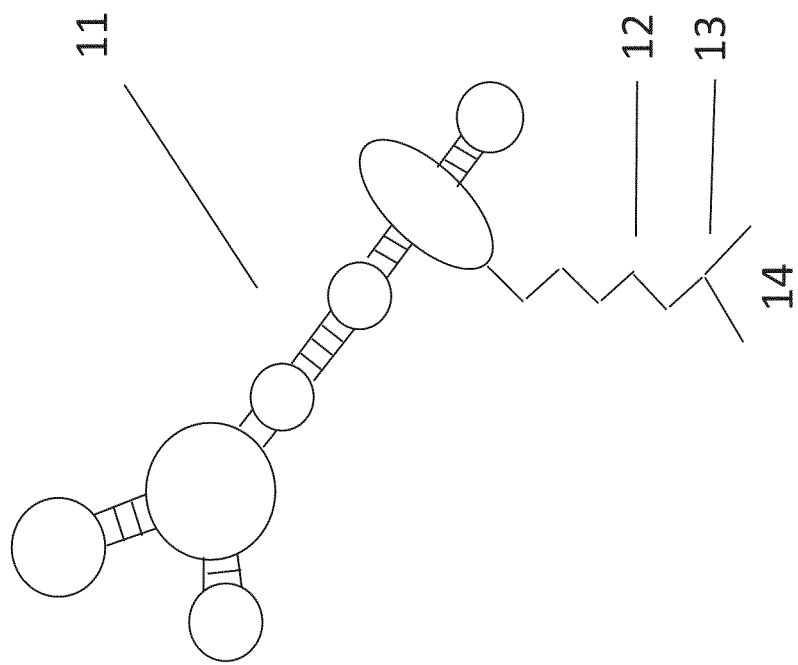

FIG. 4B is a magnified view of an individually immobilized aptamer sensor (502). A *Salmonella* enterotica (2) is visible with its binding domain on an outer membrane protein (1). An immobilized *S. Typhimurium* aptamer (11) is shown, linked via a linker (Succinic anhydride) (12) to an amino-silanization molecule (13). The amino-silanization molecule (13) is connected to a SiO2 insulator (14), a p-Si substrate (15), and finally to a conductive electrode (16) for the electronics interface. Together, these elements form the smallest working construct of the aptamer sensor plate (502). The insulation plate (17) (not shown) would be placed directly between the PCB (400) in the lid (501) and the aptamer biosensor plate (502). FIG. 4C is a diagram showing the molecular shape of the immobilized *S. Typhimurium* aptamer (11). The linker (Succinic anhydride) (12) and the amino-silanization molecule (13) are also shown in their placement and orientation. The SiO2 insulator (14) is also viewable where it is connected to the amino-silanization molecule (13).

Figure 2A:
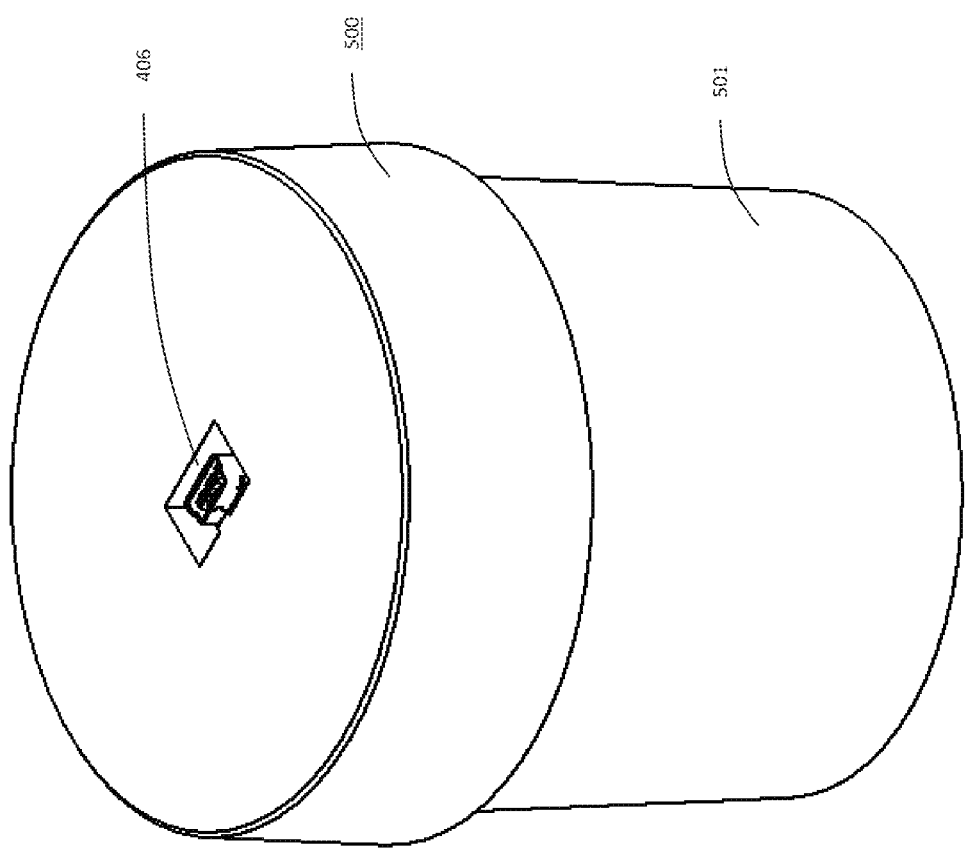
Figure 2B:
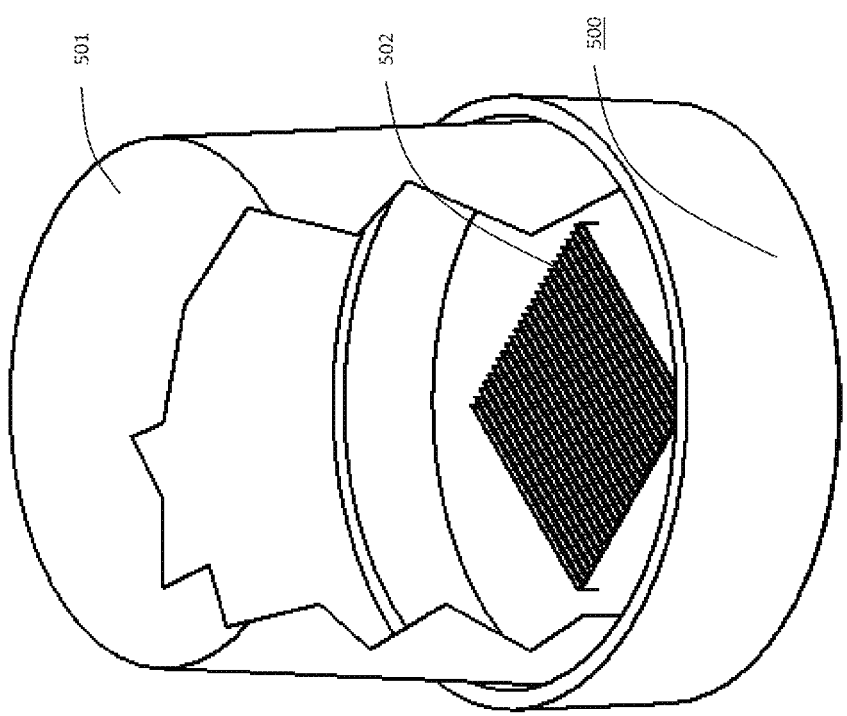
Figure 2C:
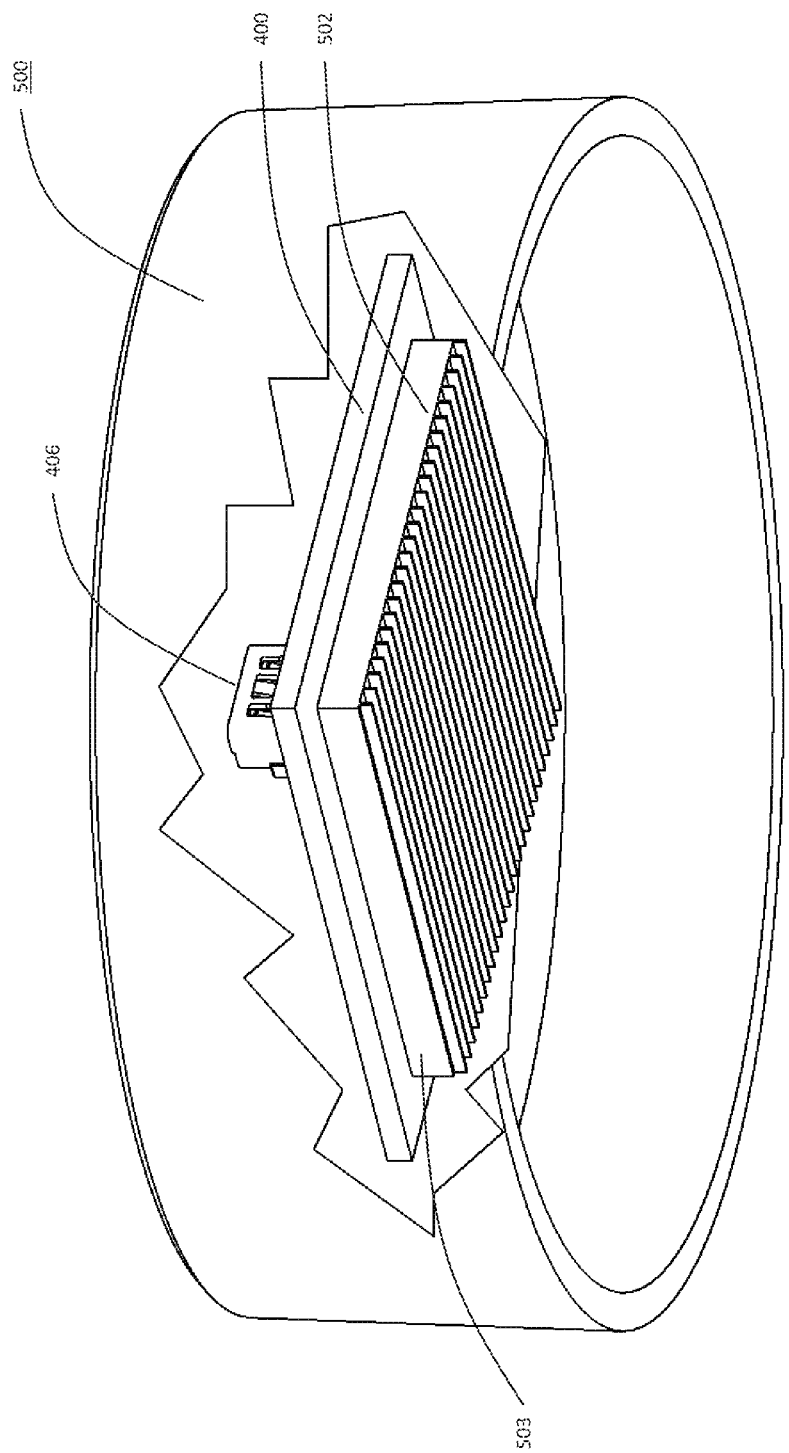
Figure 2D:
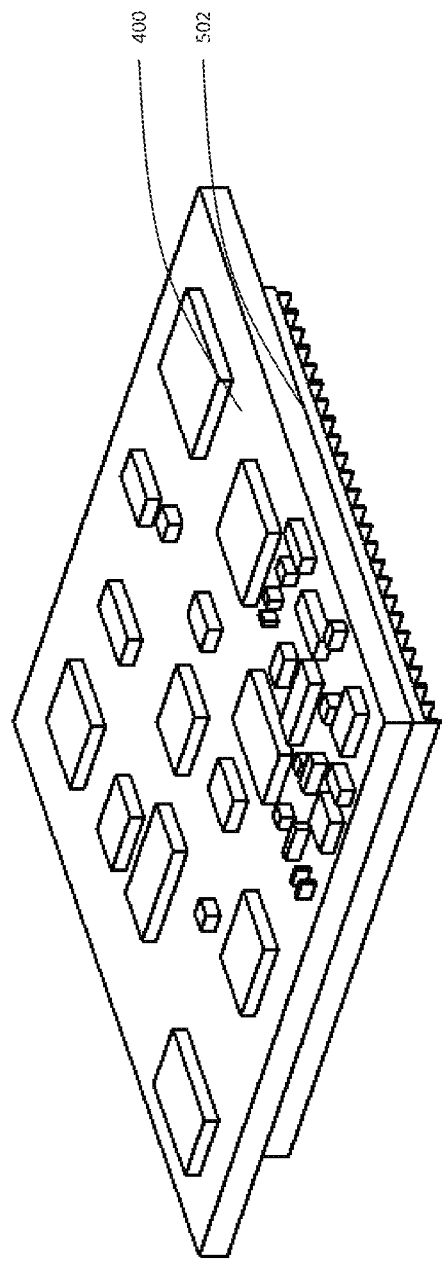
Figure 2E:
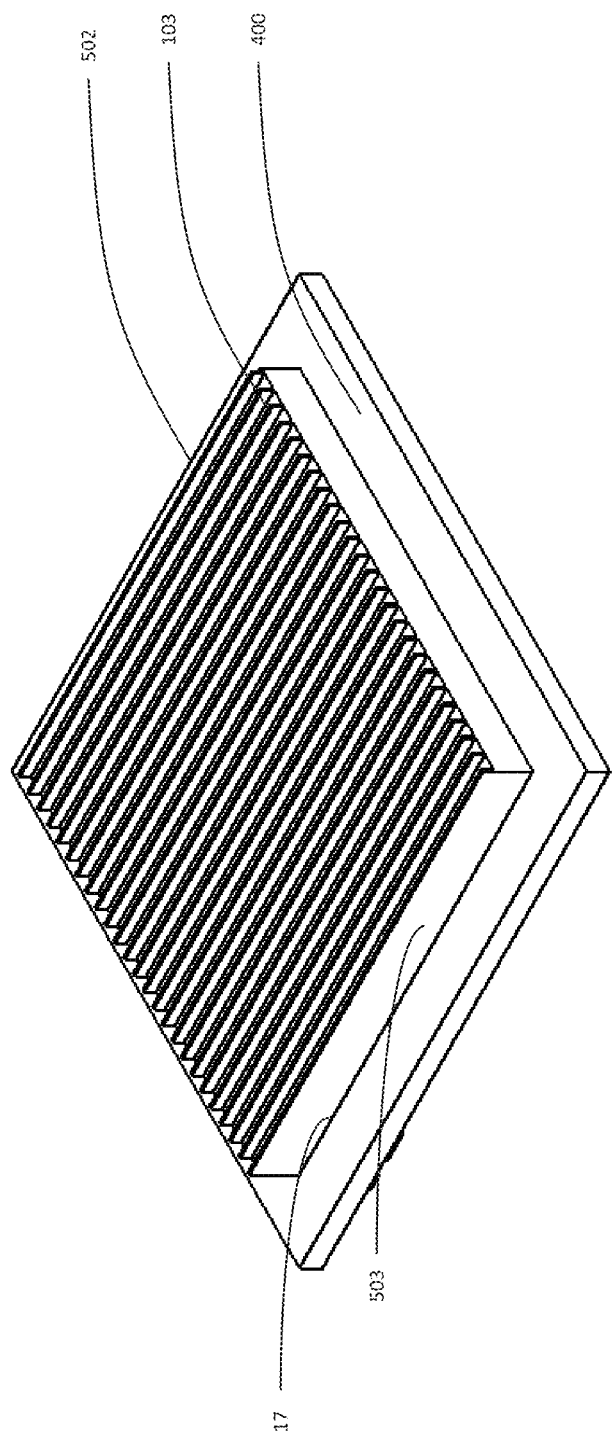
Figure 3:
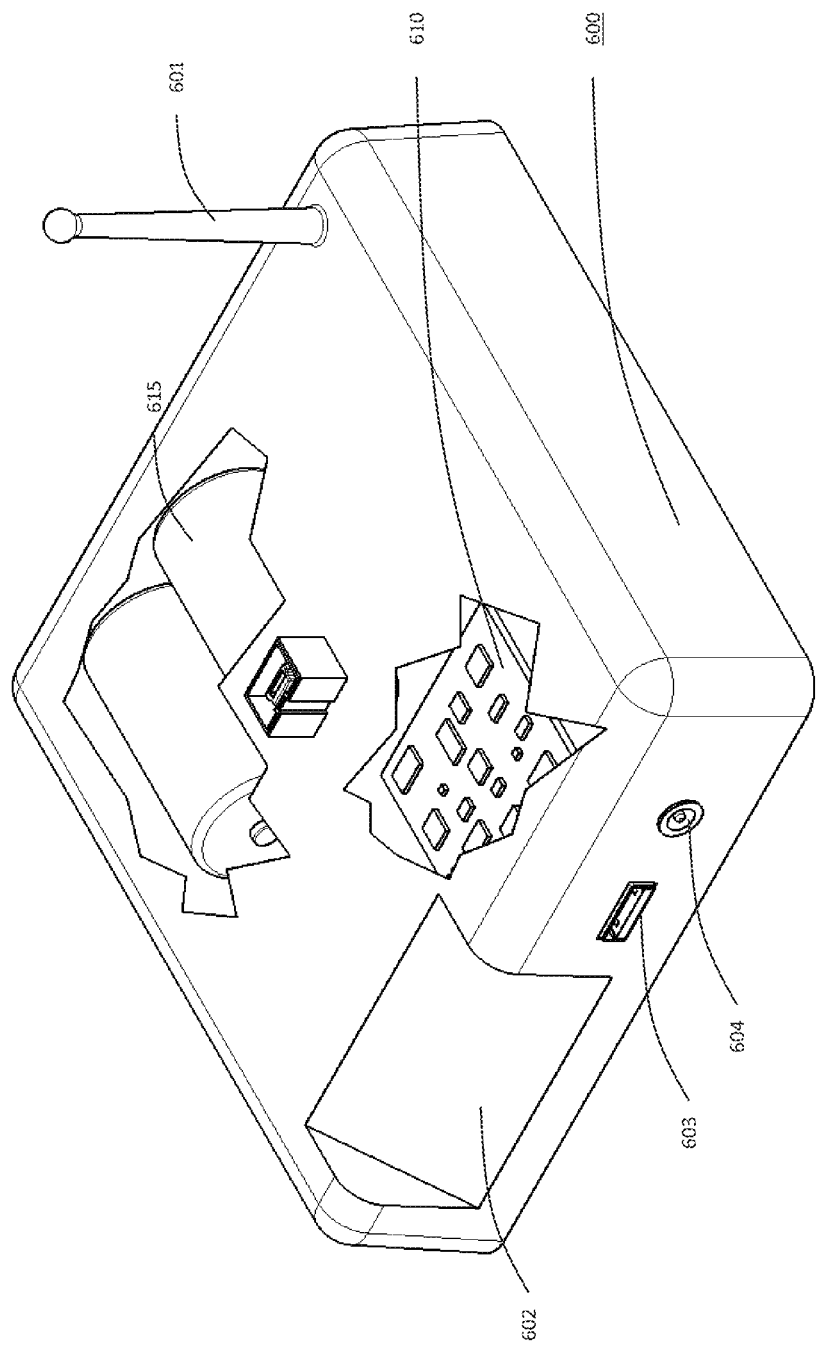
Figure 5:
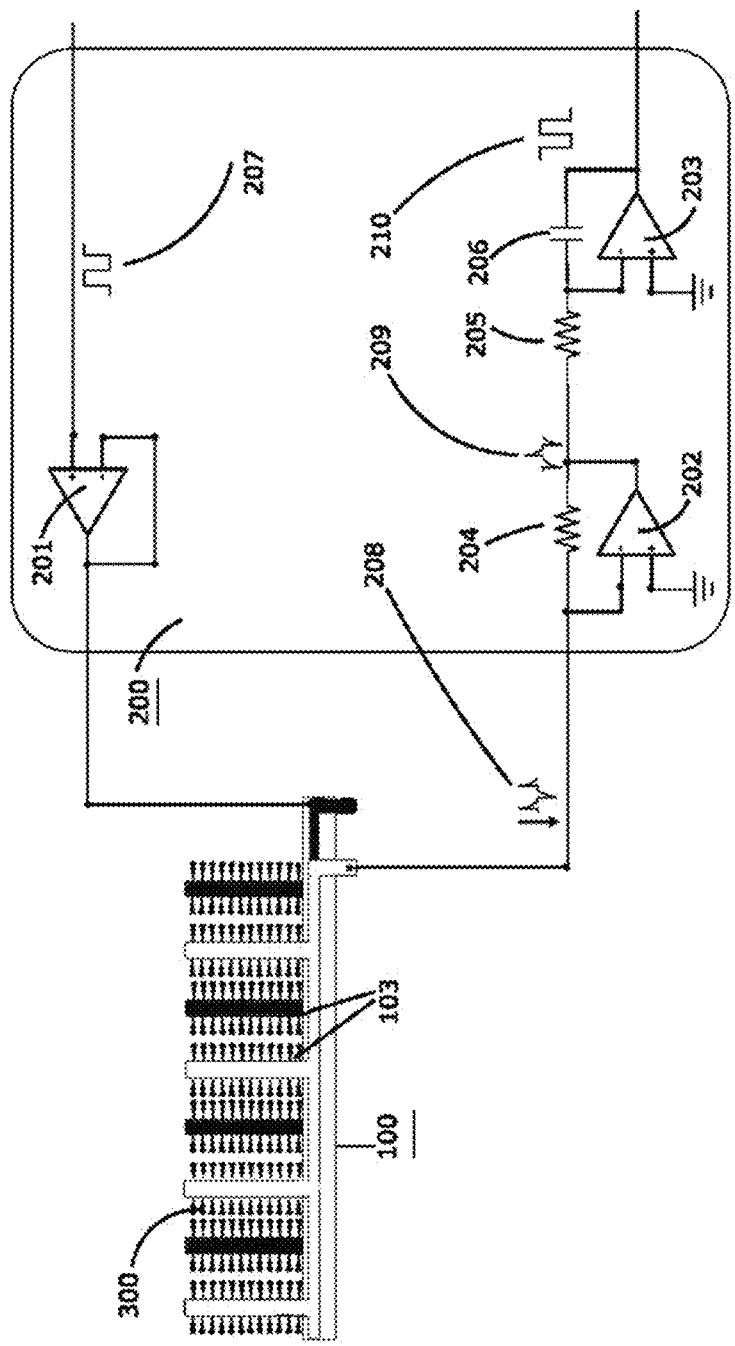

FIG. 5 is a schematic representation of the preferred embodiment of the invention depicting an equivalent electrical circuit of the capacitor array (103) shown in FIG. 2E. An effective sensor geometry Gx (300) is shown, coupled to an electrode plate assembly (100). An Op Amp buffer (201) increases the input impedance of a detector circuit (200), and ensures a near perfect square wave from an input signal (207). A current signal (208), which is proportional to the amount of hybridization of the analytes with the capture reagents, is detected at the output of circuit (200) due to its impedance. An active amplifier (202), transforms the current signal (208), into a voltage signal (209), whose area under the curve is proportional to the hybridization.

Figure 6:
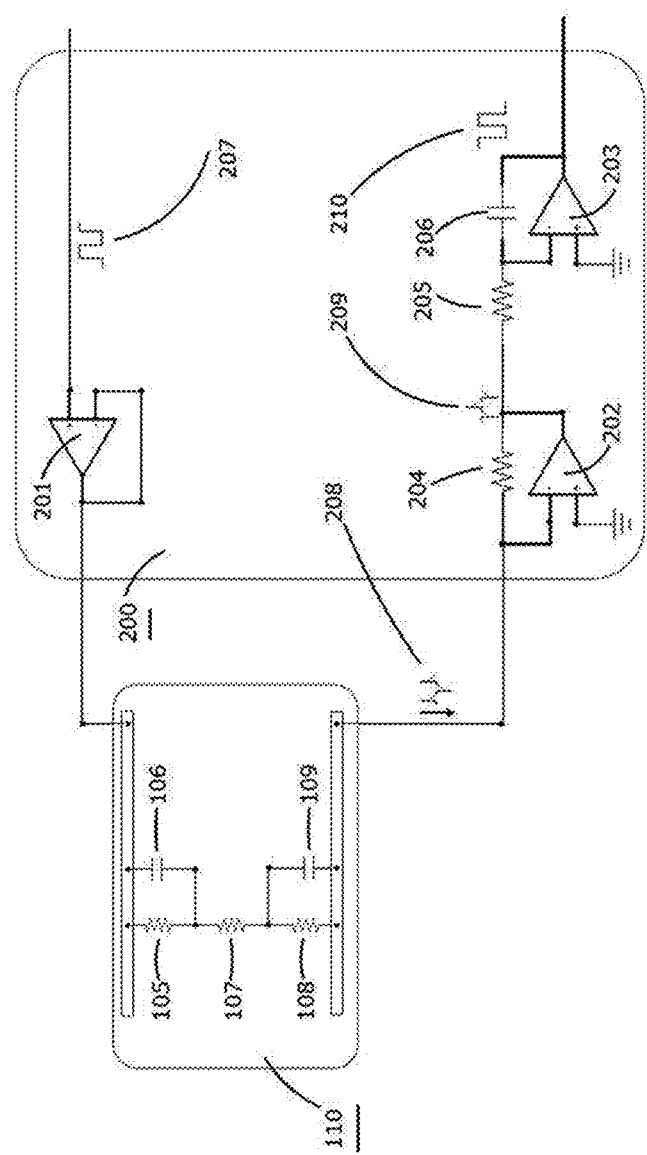

FIG. 6 is a schematic representation of the preferred embodiment of the invention depicting an equivalent electrical circuit of the capacitor array, and an alternate representation of the detector circuit shown in FIG. 5. The circuit schematic, noted by reference designator (110), comprises a resistance of the interface between electrode A and test sample solution (RA) (105), a double-layer capacitance between electrode A and test sample solution (CA) (106), the resistance (RS) (107) of the test sample solution within the sensor body (100), a resistance of electrode B/solution interface (RB) (108), and a double-layer capacitance of electrode B/solution interface (CB) (109). The capacitor array (110) forming the biosensor, is interfaced with the capacitive detector circuit (200). The Op Amp buffer (201) increases the input impedance of the detector circuit (200), and ensures a near perfect square wave from the input signal (207). A current signal (208), which is proportional to the amount of hybridization of the analytes with the capture reagents, is detected at the output of detector circuit (110) due to its impedance. The active amplifier (202) transforms the current signal (208) into a voltage signal (209), whose area under the curve is proportional to the hybridization.

Figure 7:
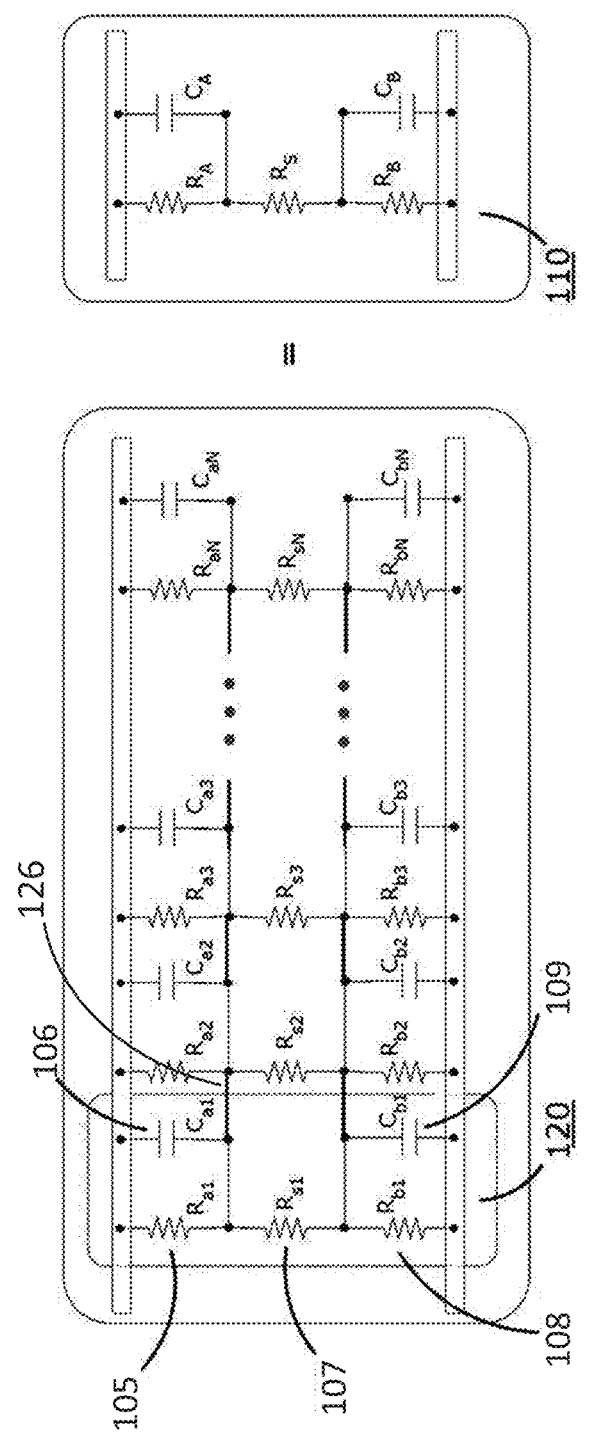

FIG. 7 shows an equivalent circuit to that of the detector circuit (110) of the *Salmonella* biosensor and how the circuit can be decomposed to model for each pair of capacitive plates (103) in the capacitor matrix array (300). Each pair of capacitive plates (103) forms an electrode-electrolyte interface with the solution which can be represented with an equivalent circuit (120). Because the solution medium is dynamic, the circuit for each plate pair is shorted at the electrode and solution interface. Thus, the equivalent circuit of the entire sensor can be written as the combined circuits of each plate pair, which is electrically in parallel to its neighbor pair. Equations 9-13 allow the parameters of the detector circuit (110) be derived from the parameters of each plate pair (120).

$$C_A = C_{a1} || C_{a2} || \ldots || C_{aN} = \sum_N C_{ai} \qquad (9)$$

$$C_B = C_{b1} || C_{b2} || \ldots || C_{bN} = \sum_N C_{bi} \qquad (10)$$

$$R_A = R_{a1} || R_{a2} || \ldots || R_{aN} = \frac{1}{\sum_N \frac{1}{R_{ai}}} \qquad (11)$$

$$R_B = R_{b1} || R_{b2} || \ldots || R_{bN} = \frac{1}{\sum_N \frac{1}{R_{bi}}} \qquad (12)$$

$$R_S = R_{s1} || R_{s2} || \ldots || R_{sN} = \frac{1}{\sum_N \frac{1}{R_{ci}}} \qquad (13)$$

Figure 8:
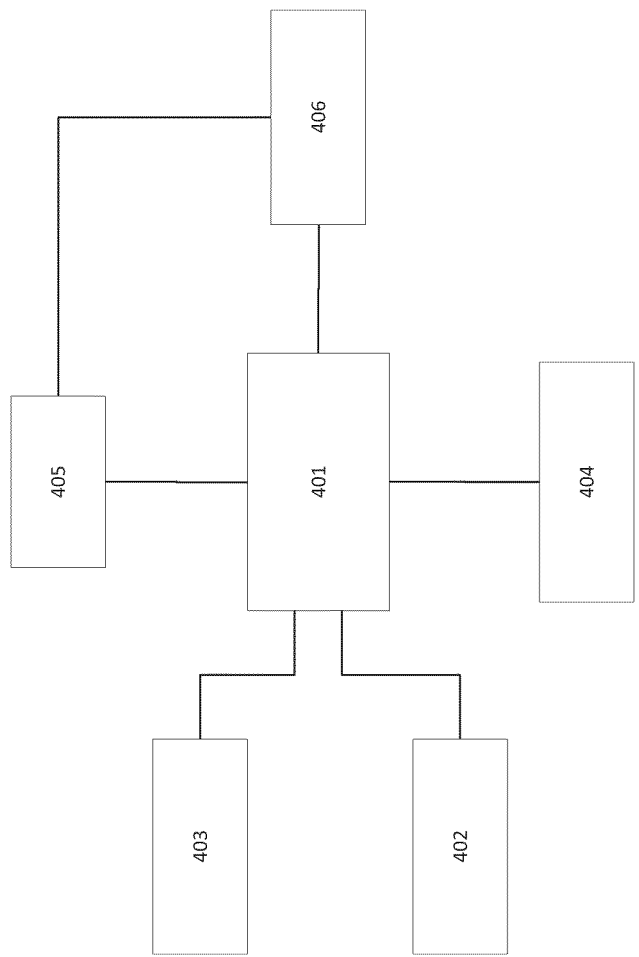

FIG. 8 is a visual schematic of a temperature sensor (403) disposed on the PCB (400) coupled within the lid (501). A microcontroller (401) in the lid (501) acts as the master control by reading a *Salmonella* aptamer sensor (402) and the temperature sensor (403) and then writing this data to a memory present on the base PCB (610) in the base station (600). An optional circulation pump (404) is also controlled by the microcontroller (401), while the power supply (405) for the cup (500) is provided by means of USB communication from the lid USB port (406) to the base station (600).

Figure 9:
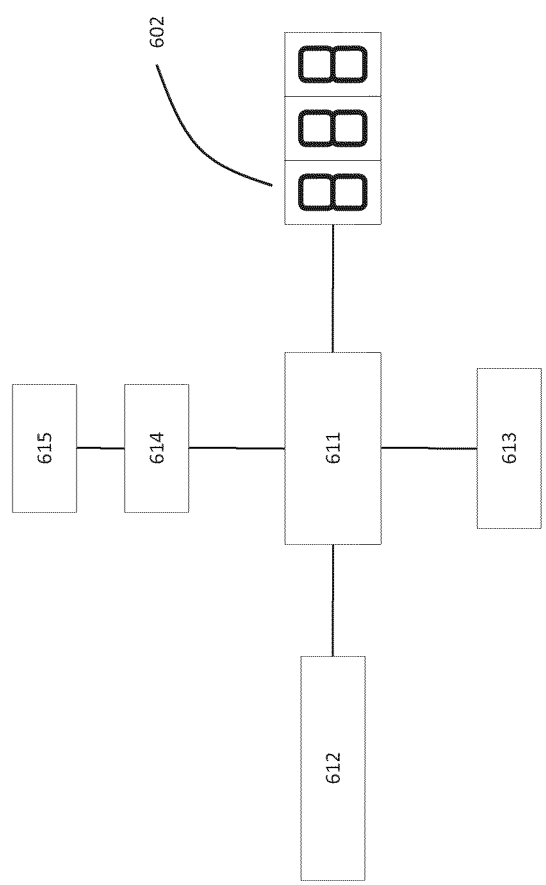

FIG. 9 is a schematic block diagram of the computations performed by a Central Processing Unit (CPU) (611) on the base PCB (610). The CPU (611) in the base station (600) communicates and commands all other aspects of the base PCB (610). Wireless communication via the antenna (601) to an external receiver (612) allows communication between the aptamer based *salmonella* detection system and a central control location such as an external computer for data collection. The lid USB communication (613) to the lid (501) provides the input from the sample analysis taking place in the cup (500). Further, a power supply (614) for the base station (600) is provided via batteries (615) under normal operation. The use of the antenna (601) and batteries (615) allows cordless and wireless use of the device.

The invention described herein is designed to be highly automated so as to allow minimal training to be needed in order to carry out the examination. For example the device can be installed on the container that is transporting the goods to be tested. The device is housed in a weatherproof box (not shown), and is attached securely to the outside of the container to travel with the goods. This would allow testing to be verified on the other end of the route, if needed.

To prepare a testing cycle, broth (such as BHI broth) will be added in a set amount to the cup (500), allowing enough room for addition of a sample of the food. The food sample is then added to the specimen cup (500). Next, the lid detection device (501) is prepared for use by pulling a plastic tabbed cover (not shown) from the aptamer sensing plate (502). Subsequently, the lid (501) is placed firmly on the specimen cup (500), and this combination unit is then turned upside down and placed into the base station (600) as seen in FIG. 1.

After this preparation procedure, the remainder of the testing is automated. Results can be wirelessly transmitted at any WiFi access point via the antennae (601), such as those present in warehouses and at weigh stations. After the testing procedure is accomplished, the cup (500) and lid (501) are disposed of, and the base station (600) is utilized with a new cup (500) and lid (501).

Standard off-the-shelf components are utilized whenever possible for the purpose of diminishing the cost of the device, while also maintaining the high level of quality and versatility that can be garnered by utilizing standardized parts. The custom components involved in the making of the device, including the base station (600), lid (501), and cup (500), are the PCB boards (610, 400), the aptamer plate (100), the software, and the various device housings.

Programming of the device can be accomplished via the USB connection (603) on the base station (600). The base (600) of the device utilizes a Liquid Crystal Display (LCD) screen (602) to output visually the state and results of the testing procedure without the need to connect to a standard personal computer. The device is programmed at a central location so that the field use of the device is as simplified as possible, and also to avoid tampering with the device via manipulation of the controls. The device may be powered by an electrical source of any kind, including the batteries (615), the DC current from a truck or car or externalized battery (not shown) attached via the power charging port (604), or by AC current from a wall socket, or other source (not shown) to the charging port (604).

In an alternative embodiment, if the device is mounted on the outside of a shipping container, the device may utilize a solar power photo-electric cell layer on the outside of the weatherproof enclosure (not shown) for the device as a power source.

Finally, the device allows for previously unavailable simplified collection of data on food spoilage. Because the device runs at all times, and utilizes a real-time clock along with a temperature sensor, the device is capable of recording conditions within the sample at all times during the transit of the device. This kind of information has not been available previously, and will allow for the designing of higher accuracy predictions in regards to food spoilage, based upon time and temperature conditions.

In summary, the disclosed invention allows for highly automated, accurate testing for *Salmonella enterica* bacteria in food sources, during transit, accomplished by lightly trained personnel, but also providing high accuracy and reasonable cost. Further, the device will collect information on *Salmonella enterica* over time and record this information, allowing for greater accuracy and more dependable results.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An electrochemical sensor array utilizing an aptamer-probe complex for detecting the presence of a target molecule, wherein the aptamer-probe complex comprises:
an aptamer capable of binding to an indicator protein and change the properties of the indicator protein; and
a recognition group capable of binding to the aptamer,
wherein the aptamer and recognition group are coupled to each other such that the binding between the aptamer and the indicator protein of the target molecule changes when the aptamer binds to the target molecule, and wherein the sensor array comprises:

a substrate;

a plurality of sealed micro machined capacitors coupled to the substrate, wherein each of the plurality of micro machined capacitors has a plurality of surfaces, at least one of the plurality of surfaces having a recognition group receptive to a target coupled to it;

a detector for sensing each of the plurality of capacitors; and a printed circuit board comprising a microcontroller coupled to the substrate, the microcontroller configured to read a result obtained from the detector, wherein the recognition groups coupled to the plurality of micro machined capacitors are responsive to *Salmonella enterica* outer membrane protein targets, wherein the substrate, printed circuit board, and plurality of micro machined capacitors are disposed within a lid of a specimen cup, the specimen cup being removably coupled to a base station through a USB connection.

2. The sensor array of claim 1 wherein the plurality of surfaces have at least one aptamer-probe complex with electrochemical affinity attractive to the target molecule coupled to it.

3. The sensor array of claim 1 wherein the plurality of capacitors forms a sensor with means to report changes in the indicator protein to the microcontroller on the printed circuit board within the lid of the specimen cup.

4. The sensor array of claim 1 where the recognition groups comprise successive layers of:

a SiO2 insulator;

an amino-silanization layer; and a Succinc anhydride linker acting as an immobilizer.

5. The sensor array of claim 1 further comprising means for analyzing and displaying the results obtained from the detector on the base station.

6. The sensor array of claim 5 further comprising a wireless antenna disposed on the base station configured to wirelessly transmit the results obtained from the detector via a WiFi network.

7. A system for *Salmonella* testing with a sensor comprising:

a specimen cup comprising a lid;

a base station;

a printed circuit board disposed in the lid of the specimen cup;

a substrate coupled to the printed circuit board;

a sealed micromachined mesh capacitor-array coupled to the substrate;

a recognition group coupled to the substrate, the recognition group being receptive to a target;

a detector for detecting the target; and a delivery system for delivering a fluid for analysis to the sensor, wherein the delivery system comprises:

an input port;

a reservoir coupled to the input port; and an output port coupled to the reservoir, wherein at least a portion of the substrate being exposed to the fluid in the reservoir, wherein the delivery system further provides for an unrestricted circulation flow of the fluid through the sensor, and wherein the specimen cup is removably coupled to the base station through a USB connection.

8. The system of claim 7 further comprising a plurality of internalized non-rechargeable batteries disposed in the base station, by a plurality of internalized rechargeable batteries disposed in the base station, or by an external AC or DC power source coupled to the base station.

9. The system of claim 7 further comprising a case configured to accommodate the system, the case configured to be coupled to the outside of a shipping container or other shipping vehicle.

10. The system of claim 9 further comprising a solar power photo-electric cell layer coupled to the system such that power is provided to the system as long as it is coupled to the outside of the shipping container or other shipping vehicle.

11. A method for testing for Salmonella in a fluid sample comprising:

exposing a sensor comprising a substrate coupled to a sealed micro machined capacitor-array to the fluid sample to be analyzed within a specimen cup;

exposing a recognition group coupled to the capacitor-array to the sample fluid;

receiving a target molecule by the recognition group;

coupling the specimen cup to a base station through a USB connection; and analyzing the target molecule to determine if the target molecule found in the sample fluid being analyzed is *Salmonella,* wherein analyzing the target molecule comprises direct actuation by an electronic means in contact with the sensor and determining one of a change in the capacitive value of the sensor, a change in impedance, or a rate of change of the system over time by a microcontroller disposed on a printed circuit board, wherein the printed circuit board is coupled to the substrate and disposed in a lid of the specimen cup.

12. The method of claim 11 further comprising recording time and temperature changes in the fluid sample, thereby enabling real-time analysis and accurate estimation of pathogen content in the sample, via a flash memory record disposed on an internalized printed circuit board within the base station.

13. The method of claim 11 further comprising powering the sensor by either a plurality of internalized non-rechargeable batteries disposed within the base station, by a plurality of internalized rechargeable batteries disposed within the base station, or by an external AC or DC power source coupled to the base station.

* * * * *